US006846918B2

(12) United States Patent
Beckvermit et al.

(10) Patent No.: US 6,846,918 B2
(45) Date of Patent: Jan. 25, 2005

(54) NUCLEOSIDE MODIFICATIONS BY PALLADIUM CATALYZED METHODS

(75) Inventors: Jeffrey T. Beckvermit, Berthoud, CO (US); Chi Tu, Louisville, CO (US)

(73) Assignee: Gilead Sciences, Inc., Foster City, CA (US)

(*) Notice: Subject to any disclaimer, the term of this patent is extended or adjusted under 35 U.S.C. 154(b) by 0 days.

(21) Appl. No.: 10/351,468

(22) Filed: Jan. 24, 2003

(65) Prior Publication Data

US 2004/0034212 A1 Feb. 19, 2004

Related U.S. Application Data

(60) Continuation of application No. 10/047,786, filed on Jan. 15, 2002, now Pat. No. 6,512,106, which is a continuation of application No. 09/495,429, filed on Jan. 31, 2000, now Pat. No. 6,355,787, which is a division of application No. 09/160,747, filed on Sep. 25, 1998, now Pat. No. 6,020,483.

(51) Int. Cl.$^7$ .......................... C07H 19/00; C07H 21/00
(52) U.S. Cl. .................... 536/22.1; 536/23.1; 536/25.3; 536/28.1; 536/28.2; 536/28.4; 536/28.6; 536/28.7
(58) Field of Search .............................. 536/22.1, 25.3, 536/28.1, 28.2, 28.4, 28.6, 28.7

(56) References Cited

U.S. PATENT DOCUMENTS

| | | | |
|---|---|---|---|
| 4,267,171 A | | 5/1981 | Bergstrom et al. |
| 4,594,339 A | | 6/1986 | Lopez et al. |
| 5,047,519 A | | 9/1991 | Hobbs, Jr. et al. |
| 5,053,499 A | | 10/1991 | Kojima et al. |
| 5,223,263 A | | 6/1993 | Hostetler et al. |
| 5,420,276 A | | 5/1995 | Norbeck |
| 5,428,149 A | | 6/1995 | Eaton |
| 5,580,972 A | | 12/1996 | Tu et al. |
| 5,596,091 A | | 1/1997 | Switzer |
| 5,719,273 A | | 2/1998 | Tu et al. |
| 6,020,483 A | * | 2/2000 | Beckvermit et al. ..... 536/27.11 |
| 6,355,787 B1 | * | 3/2002 | Beckvermit et al. ....... 536/23.1 |
| 6,512,106 B2 | * | 1/2003 | Beckvermit et al. ..... 536/26.71 |

FOREIGN PATENT DOCUMENTS

| | | |
|---|---|---|
| JP | 2-215793 | 8/1990 |
| WO | WO90/15065 | 12/1990 |
| WO | WO91/06556 | 5/1991 |
| WO | WO91/06629 | 5/1991 |
| WO | WO91/10671 | 7/1991 |
| WO | WO91/14696 | 10/1991 |
| WO | WO94/26761 | 11/1994 |

OTHER PUBLICATIONS

Agathocleous and Shaw (1991) J. Chem. Soc. Perkin Trans. 1, 10:2317–2321.
Arai and Daves (Jan. 1978) J. Am. Chem. Soc. 100:287–288.
Bergstrom et al. (1982) J. Org. Chem. 47:2174–2178.
Bergstrom and Ruth (Mar. 1976) J. Am. Chem. Soc. 98:1587–1589.
Bergstrom et al. (1981) J. Org. Chem. 46:1432–1441.
Crisp (1989) Syn. Commun. 19:2117–2123.
Crisp and Flynn (1990) Tetrahedron Lett. 31:1347–1350.
Crouch and Eaton (1994) Nucleosides & Nucleotides 13:939–944.
Dreyer and Dervan (Feb. 1985) Proc. Natl. Acad. Sci. USA 82:968–972.
Fukuda et al. (Dec. 1986) Z. Naturforsch. 41b:1571–1579.
Goodchild et al. (Sep. 1983) J. Med. Chem. 26:1252–1257.
Greene et al. (1991) *Protective Groups in Organic Synthesis*, 2$^{nd}$ Edition., John Wiley & Sons, New York, NY pp. 62–63.
Guschlbauer et al. (Jun. 1977) Nucleic Acids Research 4:1933–1943.
Hacksell and Daves, Jr. (1983) J. Org. Chem. 48:2870–2876.
Hobbs et al. (1973) Biochemistry 12:5138–5145.
Ikehara and Tada (1968) in *Synthetic Procedure in Nucleic Acid Chemistry*, Interscience Publishers/John Wiley & Sons, New York, NY, pp. 189–192.
Kao (1982) J. Org. Chem 47:1267–1277.
Larock et al. (1989) Tetrahedron Lett. 30:6629–6632.
Larock (1990) Pure & Appl. Chem. 62:653–660.
Mamos et al. (Apr. 1992) Tetrahedron Lett. 33(17):2413–2416.
Moriarty et al. (Oct. 1990) Tetrahedron Lett. 31(41):5877–5880.
Ono et al. (1994) Bioorg. & Med. Chem. Lett. 4:361–366.
Pieken et al. (Jul. 1991) Science 253:314–317.
Perlman et al. (Jun. 1985) J. Med. Chem. 28(6):741–748.
Ruth and Bergstrom (Jul. 1978) J. Org. Chem. 43:2870–2876.
Sagi et al. (Apr. 1994) J. Med. Chem. 37:1307–1311.
Schoenberg and Heck et al. (1974) J. Org Chem. 39:3327–3331.
Sessler et al. (1993) J. Am. Chem. Soc. 115:10418–10419.
Shibahara et al. (1987) Nucleic Acids Research 15:4403–4415.
Sproat et al. (1989) Nucleic Acids Research 17:3373–3384.
Tronchet et al. (1988) Nucleosides & Nucleotides 7:249–269.
Van Aerschot et al. (Oct. 1993) J. Med. Chem. 36:2938–2942.
Zhang and Daves (1993) Organometallics 12:1499–1500.

* cited by examiner

Primary Examiner—Samuel Barts
Assistant Examiner—Patrick T. Lewis
(74) Attorney, Agent, or Firm—Swanson & Bratschun, L.L.C.

(57) ABSTRACT

This invention discloses a method for the preparation of 2'-modified nucleosides, using a palladium catalyst and an alkene functionalized with a heteroatom. Included in the invention are the novel pyrimidines and purines that can be prepared according to the method of the invention and oligonucleotides containing said modified pyrimidines and purines.

9 Claims, No Drawings

NUCLEOSIDE MODIFICATIONS BY PALLADIUM CATALYZED METHODS

RELATED APPLICATIONS

This application is a continuation of Ser. No. 10/047,786, now U.S. Pat. No. 6,512,106 Issue date Jan. 28, 2003, filed Jan. 15, 2002, entitled "Nucleoside Modifications by Palladium Catalyzed Methods," which is a continuation of Ser. No. 09/495,429, now U.S. Pat. No. 6,355,787 Issue date Mar. 12, 2002, filed Jan. 31, 2000, entitled "Nucleoside Modifications by Palladium Catalyzed Methods and Compounds Produced," which is a divisional of Ser. No. 09/160,747, now U.S. Pat. No. 6,020,483 Issue date Feb. 1, 2000, filed Sep. 25, 1998, entitled "Nucleoside Modifications by Palladium Catalyzed Methods."

FIELD OF THE INVENTION

This invention relates to the field of nucleic acid chemistry, specifically to a process for preparing modified nucleosides and nucleotides. The nucleosides and nucleotides can be pyrimidines or purines. The pyrimidine compounds of the invention can be modified at the 5- or 6-position of the pyrimidine ring. The purine compounds of the invention can be modified at the 2-, 6- or 8-position of the purine ring. Preferably, the invention includes a process for preparing nucleosides and nucleotides modified at the 5-position of the pyrimidine ring and at the 2-, 6- or 8-position of the purine ring, most preferably the 8-position of the purine ring. The present invention also includes the modified nucleosides and nucleotides produced by the method and oligonucleotides containing such modified nucleosides and nucleotides. The invention also includes the use of the modified nucleosides and nucleotides of the present invention as anti-viral, anti-bacterial, anti-fungal or anti-neoplastic agents alone or as part of an oligonucleotide.

BACKGROUND OF THE INVENTION

Until quite recently, the consideration of oligonucleotides in any capacity other than strictly informational was unheard of. Despite the fact that certain oligonucleotides were known to have interesting structural possibilities (e.g., t-RNAs) and other oligonucleotides were bound specifically by polypeptides in nature, very little attention had been focused on the non-informational capacities of oligonucleotides. For this reason, among others, little consideration had been given to using oligonucleotides as pharmaceutical compounds.

There are currently at least three areas of exploration that have led to extensive studies regarding the use of oligonucleotides as pharmaceutical compounds. In the most advanced field, antisense oligonucleotides are used to bind to certain coding regions in an organism to prevent the expression of proteins or to block various cell functions. Additionally, the discovery of RNA species with catalytic functions—ribozymes—has led to the study of RNA species that serve to perform intracellular reactions that will achieve desired effects. And lastly, the discovery of the SELEX process (Systematic Evolution of Ligands by Exponential Enrichment) (Tuerk and Gold (1990) Science 249:505) has shown that oligonucleotides can be identified that will bind to almost any biologically interesting target.

The use of antisense oligonucleotides as a means for controlling gene expression and the potential for using oligonucleotides as possible pharmaceutical agents has prompted investigations into the introduction of a number of chemical modifications into oligonucleotides to increase their therapeutic activity and stability. Such modifications are designed to increase cell penetration of the oligonucleotides, to stabilize them from nucleases and other enzymes that degrade or interfere with the structure or activity of the oligonucleotide analogs in the body, to enhance their binding to targeted RNA, to provide a mode of disruption (terminating event) once sequence-specifically bound to targeted RNA and to improve their pharmacokinetic properties. For example, PCT Patent Application Publication No. WO 91/14696, entitled "Oligonucleotide-Transport Agent Disulfide Conjugates," describes a method for chemically modifying antisense oligonucleotides to enhance entry into a cell.

A variety of methods have been used to render oligonucleotides resistant to degradation by exonucleases. PCT Patent Application Publication No. WO 90/15065, entitled "Exo nuclease-Resistant Oligonucleotides and Methods for Preparing the Same," describes a method for making exonuclease-resistant oligonucleotides by incorporating two or more phosphoramidite and phosphoromonothionate and/or phosphorodithionate linkages at the 5' and/or 3' ends of the oligonucleotide. PCT Patent Application Publication No. WO 91/06629, entitled "Oligonucleotide Analogs with Novel Linkages," describes oligonucleotide compounds with one or more phosphodiester linkages between adjacent nucleotides replaced by a formacetal/ketal type linkage which are capable of binding RNA or DNA.

A common strategy for the stabilization of RNA against endonucleolytic cleavage is to modify the 2'-position of ribonucleotides. Interference with base recognition by enzymes can be used to approach stabilization against base-specific endonucleolytic cleavage. Several strategies for this modification are known, including modification with 2'-amino and 2'-fluoro (Hobbs et al. (1973) Biochemistry 12:5138; Guschlbauer et al. (1977) Nucleic Acids Res. 4:1933), and 2'-OCH$_3$(Shibahara et al. (1987) 15:4403; Sproat et al. (1989) Nucleic Acids Res. 17:3373). PCT Patent Application Publication No. WO 91/06556, entitled "2' Modified Oligonucleotides," describes nuclease-resistant oligomers with substituents at the 2' position. PCT Patent Application Publication No. WO 91/10671, entitled "Compositions and Methods for Detecting and Modulating RNA Activity and Gene Expression," describes antisense oligonucleotides chemically modified at the 2' position and containing a reactive portion capable of catalyzing, alkylating, or otherwise effecting the cleavage of RNA, a targeting portion, and a tether portion for connecting the targeting and reactive portions.

The 5-position of pyrimidines may also be chemically modified. The introduction of modifications at the C-5position of pyrimidines may be envisioned to interfere with the recognition by pyrimidine specific endonucleases. However, this concept is not as clear cut as the modification of the 2'-position of ribonucleotides. The first examples of 5-position pyrimidine modifications were demonstrated by Bergstrom (Bergstrom et al. (1976) J. Am. Chem. Soc. 98:1587, (1978) J. Org. Chem. 43:2870, (1981) J. Org. Chem. 46:1432 and 2870, (1982) J. Org. Chem. 47:2174) and Daves (Arai and Daves (1978) J. Am. Chem. Soc. 100:287; Hacksell and Daves (1983) J. Org. Chem. 48:2870). Bergstrom and Daves used 5-mercurial-deoxyuridine compounds, the same as those used by Dreyer and Dervan (1985) Proc. Natl. Acad. Sci. USA 82:968, to tether functional groups to oligonucleotides. A superior method for 5-position modification of pyrimidines is described in U.S. patent application Ser. No. 08/076,735, filed Jun. 14, 1993, entitled "Method for Palladium Catalyzed Carbon-Carbon Coupling and Products," now U.S. Pat. No. 5,428,149 and U.S. patent application Ser. No. 08/458,421, filed Jun. 2, 1995, entitled "Palladium Catalyzed Nucleoside Modifications Using Nucleophiles and Carbon Monoxide," now U.S. Pat. No. 5,719,273, each of which is herein incorporated by reference in its entirety.

A method for simple carbon-carbon coupling reactions to the 5-position of uridines is described in the work of Crisp (1989) Syn. Commun. 19:2117. Crisp forms deoxyuridines functionalized at the 5-position by reacting protected 5-iodo-2'-deoxyuridine with alkenylstannanes in acetonitrile in the presence of a Pd (II) catalyst.

To date, very little work has been done to modify purine nucleosides using palladium catalysis. Van Aeroschot et al. (1993) J. Med. Chem 36:2938–2942, report that 2-, 6- and 8-halogenated adenosines can be modified with symmetric organotin reagents. However, symmetric organotin compounds are not widely available. Sessler et al. (1993) J. Am. Chem. 115:10418–10419, describe the arylation of protected 8-bromoguanosine with 4-tributyltinbenzaldehyde. Using this procedure, however, a significant amount of starting material (28%) was unreacted. A superior method for modifying purine nucleosides using palladium catalysts is described in U.S. patent application Ser. No. 08/347,600, filed Dec. 1, 1994, entitled "Purine Nucleoside Modifications by Palladium Catalyzed Methods," now U.S. Pat. No. 5,580,972, and U.S. patent application Ser. No. 08/458,421, filed Jun. 2, 1995, entitled "Palladium Catalyzed Nucleoside Modifications Using Nucleophiles and Carbon Monoxide," now U.S. Pat. No. 5,719,273, each of which is herein incorporated by reference in its entirety.

Additionally, very little work has been done in the area of palladium catalyzed amidations. Schoenberg et al. (1974) J. Org. Chem. 39:3327, describe amidation of aryl and alkenyl halides, however, this work does not include nucleoside substrates or the use of a PdL$_4$ catalyst.

The palladium-catalyzed coupling of allylic and non-allylic unsaturated alcohols with aryl halides has been explored for a number of years. (See, Kao et al. (1982) J. Org. Chem. 47:1267; Larock et al. (1989) Tetrahedron Lett. 30:6629; Larock (1990) Pure & Appl. Chem. 62:653–660). This reaction provides a method for the preparation of long chain aryl substituted aldehydes and ketones as illustrated below.

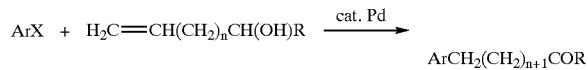

This reaction has been determined to proceed by the arylpalladation of the alkene, palladium migration and finally palladium hydride elimination to an enol which tautomerizes to the observed carbonyl product. To date, this reaction has not been extended to the functionalization of nucleosides.

SELEX™ (Systematic Evolution of Ligands for EXponential Enrichment) is a method for identifying and producing nucleic acid ligands, termed "nucleic acid antibodies" or "aptamers," e.g., nucleic acids that selectively bind to target molecules (Tuerk and Gold (1990) Science 249:505). The method involves selection from a mixture of candidates and step-wise iterations of structural improvement, using the same general selection theme, to achieve virtually any desired criterion of affinity and selectivity. Starting from a mixture of nucleic acids, the method includes steps of contacting the mixture with the target under conditions favorable for interaction, partitioning non-interacting nucleic acids from those nucleic acids which have interacted with the target molecules, dissociating the nucleic acid-target pairs, amplifying the nucleic acids dissociated from the nucleic acid-target pairs to yield a mixture of nucleic acids enriched for those which interact with the target, then reiterating the steps of interacting, partitioning, dissociating and amplifying through as many cycles as desired.

The methods of the present invention may be combined with the SELEX process (See U.S. patent application Ser. No. 07/714,131, filed Jun. 10, 1991, entitled "Nucleic Acid Ligands," now U.S. Pat. No. 5,475,096, which is a continuation-in-part of U.S. patent application Ser. No. 07/536,428, filed Jun. 11, 1990, entitled "Systematic Evolution of Ligands by Exponential Enrichment," now abandoned, each of which is specifically incorporated herein by reference in its entirety) or the parallel SELEX process (See U.S. patent application Ser. No. 08/309,245, filed Sep. 20, 1994, entitled, "Parallel SELEX," now U.S. Pat. No. 5,723,289; U.S. patent application Ser. No. 08/618,700, filed Mar. 20, 1996, entitled "Parallel SELEX," each of which is specifically incorporated by this reference in its entirety) to produce nucleic acids containing modified nucleotides. The presence of modified nucleotides may result in nucleic acids with an altered structure exhibiting an increased capacity to interact with target molecules. The steric and electronic influence of modified nucleotides may also act to prevent nuclease degradation.

SUMMARY OF THE INVENTION

The present invention describes a novel method for introducing chemical moieties at various positions of nucleoside rings utilizing a palladium catalyst and an unsaturated molecule functionalized with a heteroatom, such as oxygen, nitrogen or sulfur or an aromatic moiety. In a preferred embodiment, the modifications are at the 5- or 6-position of a pyrimidine ring or at the 2-, 6- or 8-positions of a purine ring. Most preferably the modifications are at the 5-position of the pyrimidine ring and at the 8-position of the purine ring. Particularly preferred modifications of the nucleoside ring include the introduction of an aldehyde, ketone, ester, amide, thioester or sulfine moiety.

This invention includes a reaction scheme for producing a wide variety of modified nucleoside and nucleotide molecules. A key element in the production of the modified nucleosides and nucleotides is the use of a palladium catalyst in conjunction with an allylic or nonallylic functionalized alkene. The functional group can be a heteroatom, including but not limited to oxygen, sulfur or nitrogen or it can be a substituted or unsubstituted aromatic moiety.

More specifically, the invention provides a method for the preparation of a modified nucleoside or nucleotide comprising the steps of reacting a nucleoside starting material containing a leaving group attached to a carbon atom of the nucleoside starting material with an allylic or nonallylic functionalized alkene, wherein said functional group is an alcohol, aldehyde, ketone, ester, amine, amide, thiol, thioester or a substituted or unsubstituted aromatic moiety in the presence of a palladium catalyst; and isolating the modified nucleoside or nucleotide.

Included within the scope of this invention are the modified nucleosides and nucleotides prepared according to the method of the invention and oligonucleotides comprised of at least one of such modified nucleosides or nucleotides.

This invention further includes a method of preparing stabilized nucleic acids wherein the modified nucleoside or nucleotide is coupled to a sugar modified at the 2'-position or the 3'-position.

The modified nucleosides and nucleotides of the invention have many uses including, but not limited to use as anti-viral, anti-bacterial, anti-fungal, or anti-neoplastic agents and use as part of an oligonucleotide.

DETAILED DESCRIPTION OF THE INVENTION

The present invention includes a method for modifying a nucleoside ring by reacting a nucleoside starting material with an allylic or nonallylic, functionalized alkene, wherein said functional group is a heteroatom, including but not limited to oxygen, nitrogen, sulfur or a substituted or an unsubstituted aromatic moiety in the presence of a palladium catalyst. The invention includes the modifications of both pyrimidines and purines. The pyrimidines have the following structures and conventional numbering.

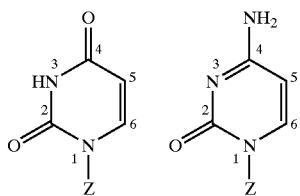

wherein Z is selected from H, ribose, deoxyribose, dideoxyribose, or any suitable derivatives thereof, such as a ribose or 2'-deoxyribose, wherein the hydroxyl groups have been partially or fully protected including, but not limited to 2'-deoxy-2'-fluoro-ribose or 2'-deoxy-2'-amino-ribose. The pyrimidine ring can be modified at the 5- or 6-position; most preferably the 5-position is modified.

The purines have the following structures and conventional numbering.

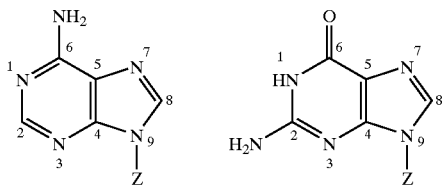

wherein Z is selected from H, ribose, deoxyribose, dideoxyribose, or any suitable derivatives thereof, such as a ribose or 2'-deoxyribose, wherein the hydroxyl groups have been partially or fully protected including, but not limited to 2'-deoxy-2'-fluoro-ribose or 2'-deoxy-2'-amino-ribose. The purine can be modified at positions 2-, 6- and 8- of the purine ring; most preferably the 8-position is modified.

The method of this invention provides nucleoside and nucleotide derivatives bearing functional groups with variable carbon chain lengths in a single step. Introduction of a variety of modifications to the nucleoside ring are contemplated by this invention. Particularly preferred modifications to the nucleoside ring include the introduction of an aldehyde, ketone, amide, thioester or sulfine moiety.

The present invention extends to all novel compounds that can be prepared according to the methods of the present invention. The present invention also includes oligonucleotides that contain one or more of the novel substituted nucleosides and nucleotides of this invention. The present invention also includes the use of the modified nucleosides and nucleotides in various pharmaceutical areas, particularly as anti-virals, anti-bacterials, anti-fungals and anti-neoplastics.

The general reactions of the present invention can be characterized as follows.

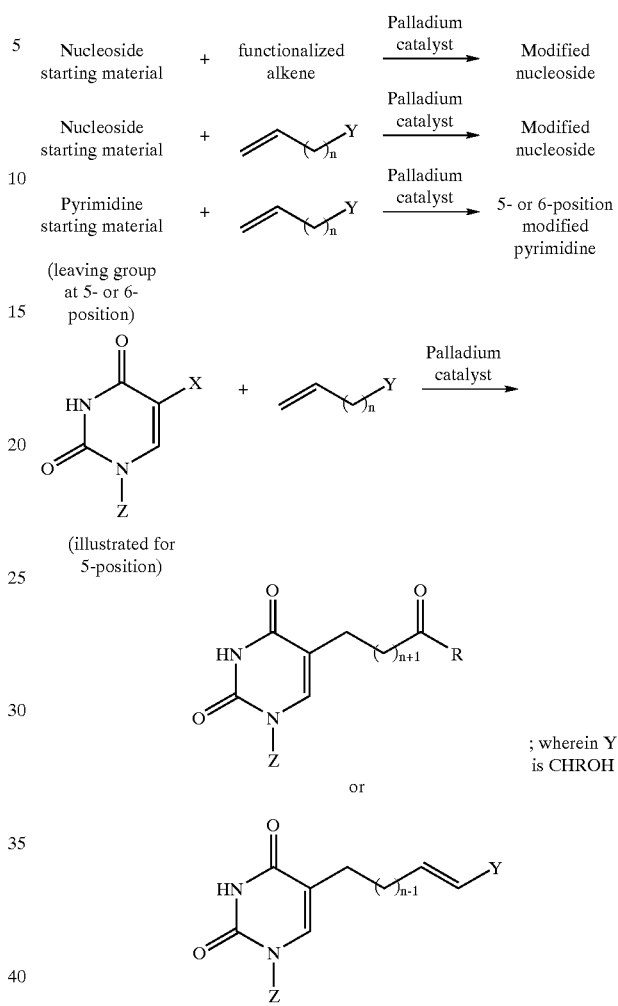

wherein

X is a leaving group, preferably a halogen;

Y is selected from the group consisting of an alcohol, ketone, aldehyde, cyanate, ester, amide, aryl, heterocycle;

Z is selected from the group consisting of H, ribose, deoxyribose, dideoxyribose, or derivatives thereof;

R is selected from the group consisting of H, substituted or unsubstituted alkyl, alkenyl and aryl; and n is an integer from 0–15.

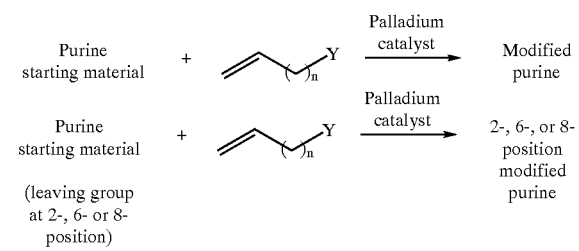

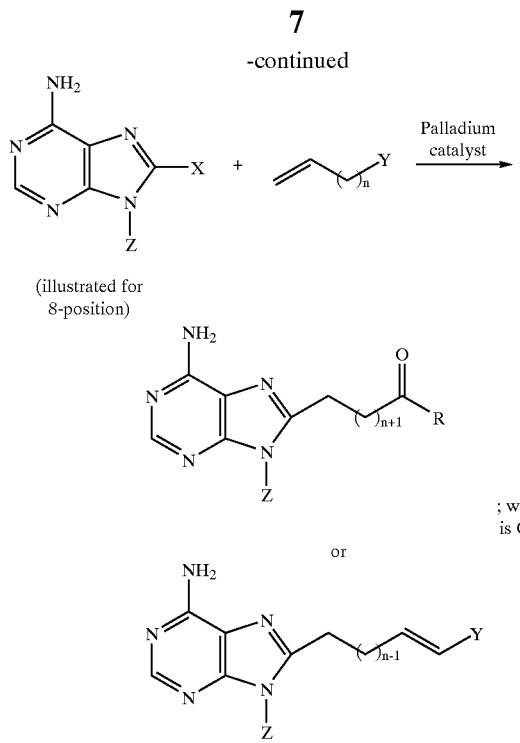

(illustrated for 8-position)

; wherein Y is CHROH or wherein
X is a leaving group, preferably a halogen;
Y is selected from the group consisting of an alcohol, ketone, aldehyde, cyanate, ester, amide, aryl, heterocycle;
Z is selected from the group consisting of H, ribose, deoxyribose, dideoxyribose, or derivatives thereof;
R is selected from the group consisting of H, substituted or unsubstituted alkyl, alkenyl and aryl; and
n is an integer from 0–15.

Certain terms used to describe the invention herein are defined as follows.

"Nucleoside starting material" is defined herein as any nucleoside base, nucleoside or nucleotide which has an attached leaving group (X). Nucleoside starting materials include all nucleosides, both naturally occurring and non-naturally occurring. Preferably, nucleoside starting materials include purines and pyrimidines, which include uracil, thymine, cytosine, adenine and guanine starting materials. The leaving group can be attached to any free carbon on the nucleoside or nucleotide base. The leaving group is displaced during the catalysis reaction and replaced by an allylic or nonallylic functionalized alkene to yield the modified nucleoside or nucleotide base. The functional group can be a heteroatom, such as oxygen, nitrogen or sulfur or a substituted or unsubstituted aromatic moiety. The nucleoside starting material can have a sugar moiety attached in the form of a ribose, deoxyribose, dideoxyribose, or any suitable derivatives thereof, such as a ribose or 2'-deoxyribose wherein the hydroxyl groups have been partially or fully protected.

"Pyrimidine starting material" is defined herein as a pyrimidine base, pyrimidine nucleoside or pyrimidine nucleotide which has an attached acceptable leaving group (X). Pyrimidine starting materials include all pyrimidines, both naturally occurring and non-naturally occurring. Preferably, pyrimidine starting materials include uracil, thymine and cytosine. The leaving group can be attached to any free carbon on the base of the nucleoside, preferably at the 5- or 6-position. The most preferred attachment is at the 5-position of the pyrimidine ring. The leaving group is displaced during the catalysis reaction and replaced by an allylic or nonallylic functionalized alkene to yield the modified nucleoside or nucleotide base. The functional group can be a heteroatom, such as oxygen, nitrogen or sulfur or a substituted or unsubstituted aromatic moiety. The pyrimidine starting material can have a sugar moiety attached in the form of a ribose, deoxyribose, dideoxyribose, or any suitable derivatives thereof, such as a ribose or 2'-deoxyribose wherein the hydroxyl groups have been partially or fully protected.

"Purine starting material" is defined herein as a purine base, purine nucleoside or purine nucleotide which has an attached acceptable leaving group (X). Purine starting materials include adenine and guanine starting materials. The leaving group can be attached to any carbon atom of the base of the purine, preferably at the 2-, 6- or 8-position of the purine ring. The most preferred attachment is at the 8-position. The acceptable leaving group is displaced during the catalysis reaction and replaced by an allylic or nonallylic functionalized alkene to yield the modified nucleoside or nucleotide base. The functional group can be a heteroatom, such as oxygen, nitrogen or sulfur or a substituted or unsubstituted aromatic moiety. The purine starting material can have a sugar moiety attached in the form of a ribose, deoxyribose, dideoxyribose, or any suitable derivatives thereof, such as a ribose or 2'-deoxyribose wherein the hydroxyl groups have been partially or fully protected.

"Oligonucleotide" refers to a polynucleotide formed from a plurality of linked nucleotide units as defined above. The nucleotide units each include a nucleoside unit linked together via a phosphate linking group. The term oligonucleotide also refers to a plurality of nucleotides that are linked together via linkages other than phosphate linkages. The oligonucleotide may be naturally occurring or non-naturally occurring. In a preferred embodiment the oligonucleotides of this invention have between 1–1,000 nucleotides.

"Leaving group" is defined herein as a group which is a suitable counterion for palladium, and is designated herein as X. In the most general embodiments of this invention, X is any of a number of acceptable leaving groups well known to those skilled in the art. Acceptable leaving groups include, but are not limited to halogens, acetate, trifluoroacetate, trifluoromethyl sulfonate, tosylate, methane sulfonate and boronic esters and acids. In a preferred embodiment, X is a halogen and in the most preferred embodiment X is bromine or iodine. The leaving group is attached to the carbon atom of the purine or pyrimidine starting material by methods known to one of ordinary skill in the art.

As used herein the term "functionalized alkene" can be defined by the following general structure:

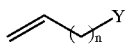

wherein
Y is selected from the group consisting of —CHROH, —C(O)R, —COOR, —C(O)NRR', —CN, a substituted or unsubstituted aryl or heterocyle, selected from the group consisting of benzene, phenol, pyridine, tetrazole;
R and R' are independently selected from the group consisting of H, substituted or unsubstituted alkyl, alkenyl and aryl; and
n is an integer from 0–15.

In a preferred embodiment of the invention the functional group (Y) is selected from the group consisting of —CH$_2$OH, —CHROH, —C(O)R, —COOR, C(O)NH$_2$ and C(O)NHR.

The R groups of the functionalized alkenes can be substituted with various functional groups which can be used to introduce a broad array of functional capabilities to the nucleosides prepared by this method. These functional groups can include, among others: amides, esters, nitrites, nitro groups, ureas, halides, cyanates, alcohols, amines, ethers, thiols, aryl substituents, etc. as recognized by those of ordinary skill in the art. Any replacement of a hydrogen on the functionalized alkene is referred to as a "substitution" for the purposes of definition.

In the most preferred embodiments of the invention, the functionalized alkenes are selected from the following group:

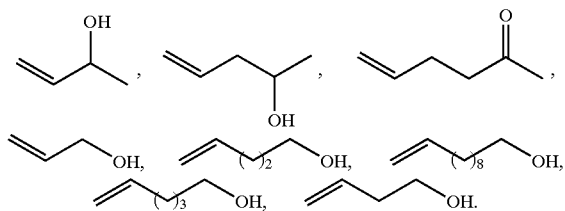

As stated above, this reaction proceeds by the arylpalladation of the alkene, palladium migration and finally palladium hydride elimination. In the case in which the functionalized alkene is a primary or secondary alcohol, the enol is formed which tautomerizes to the carbonyl product, an aldehyde or ketone, respectively.

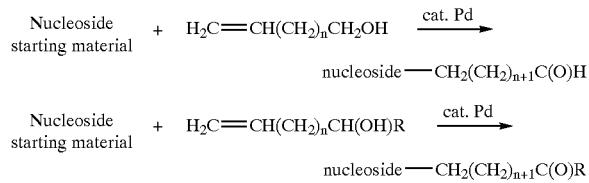

wherein R is as defined above. In the case in which the functionalized alkene is a compound that cannot be oxidized, such as a ketone, ester, cyanate, heterocycle, amide or aryl group the product of the reaction is the α, β-unsaturated compound as illustrated below for a ketone.

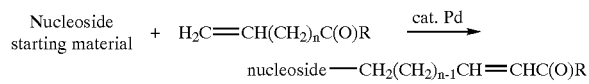

The palladium catalyst of the present invention may be characterized most generally as $PdL_4$ or $PdL_3$, where L is one of any number of commonly employed ligands of palladium. The palladium catalyst can be pre-made (e.g., $PdL_4$, wherein L is triphenyl phosphine, etc.) or made in situ from Pd(0) or Pd(II) as is known to one of ordinary skill in the art (e.g., [bis(benzylideneacetone)Pd(0)], $Pd(OAc)_2$, etc.). $PdL_4$ is the preferred palladium catalyst of the invention. It is within the skill and knowledge of those skilled in the art to recognize the various ligands that may be employed. Examples of common ligands (L) include, but are not limited to, $PPh_3$(triphenyl phosphine), $(o-tol)_3P$, $P(m-NaSO_3Ph)_3$, and

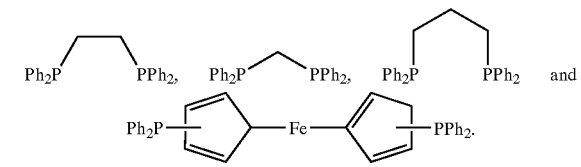

In the preferred embodiments of the catalytic species of this invention L=tris(dibenzylideneacetone)dipalladium (dba). The preparation of certain catalysts of the present invention is described in U.S. application Ser. No. 08/076,735, filed Jun. 14, 1993, entitled "Method for Palladium Catalyzed Carbon-Carbon Coupling and Products," now U.S. Pat. No. 5,428,149, which is incorporated herein by reference in its entirety.

In certain embodiments, it may be advantageous to include basic, non-nucleophilic components in the reaction. Examples of desirable bases include, but are not limited to DBU, $Na_2CO_3$, $NaHCO_3$, NaOAc, $Li_2CO_3$, LiOAc, LiCl, $Et_3N$ and $EtN(iPr)_2$. Acceptable solvents for the reaction include acetonitrile, dioxane, acetone, ethyl acetate, benzene, DMF, dimethylacetamide, DMSO, THF, hexamethylphosphoramide (HMPA), and hexamethylphosphoroustriamide (HMPT). The temperature ranges for the reaction typically are between 40° C. and 100° C., however, other suitable temperature ranges are also contemplated.

The modified nucleosides and nucleotides of the present invention are contemplated for use in oligonucleotides. Standard techniques for incorporation of nucleosides into oligonucleotides can be used with the modified nucleosides of the invention. The modified nucleosides are suitable for in vitro transcription procedures. The oligonucleotides containing the modified nucleosides have a number of various utilities. Specifically, the oligonucleotides interact with biological targets or have facilitating properties. The oligonucleotides can be useful in various diagnostic applications as well.

The nucleosides may also show antineoplastic, antibacterial, antifungal or antiviral activity. The nucleosides may also demonstrate other therapeutic properties. Standard assays are known to one of ordinary skill for determination of such activities. Formulation and administration routes are well known to those of ordinary skill in the art. Additionally, prodrug technology can be used as a delivery system for the nucleosides of the invention. Particularly, the nucleosides can be attached to lipids to improve pharmacology and oral availability, among other characteristics. Specifically, 5'-diacylglycero- or dialkylglycerophosphate-derivatives of the nucleosides of the invention are useful. These modified nucleosides are particularly interesting for antiviral applications. The diacylglycerophosphates of nucleosides and non-nucleosides have been used for modulation of pharmcokinetic behavior, modulation of bioavailability, and modulation of toxicity as described in U.S. Pat. No. 5,223,263, which is herein incorporated by reference.

Stability towards endo-nucleolytic degradation in serum can be achieved by introducing 2'-deoxy-2'-fluoro- or 2'-deoxy-2'-aminonucleosides to the pyrimidine positions of nucleic acid ligands (Pieken et al. (1991) Science 253:314). The modified nucleosides of the present invention may also be coupled with 2' substituted species that would also be useful in a variety of situations. The incorporation of halogenated nucleosides may also prove valuable for enhanced ligand-target interaction.

The following example is illustrative of preferred embodiment of methods of preparation and products of the invention and is not to be construed as limiting the invention thereto.

EXAMPLE

The following general procedures were followed to produce the modified nucleosides of Table 2. The $^1$H spectra were obtained using a Bruker 300 ARX.

General procedure for palladium catalyzed coupling reaction. Under an argon atmosphere, 5'-DMT-5-I-dU (0.5 mmoles), Pd$_2$(dba)$_3$(0.025 mmoles), Bu$_4$NCl (0.5 mmoles), LiOAc (1.25 mmoles), LiCl (0.5 mmoles), DMF (1 mL) and olefin (0.45 mmoles) were added sequentially to a 5 mL flask. The sealed flask was placed in an oil bath and the contents stirred at 60° C. for 18 hours. The mixture was then evaporated to dryness under reduced pressure. The crude product mixture was brought up in EtOAc and washed four times with NH$_4$Cl, followed by water and brine. The EtOAc layer was then dried over MgSO$_4$ and evaporated to dryness. The product was purified using silica gel flash chromatography with an elution gradient of 80% EtOAc/ 0.5% Et$_3$N/ hexane to 78% EtOAc/2% MeOH/ 0.5% Et$_3$N/hexane. The nucleoside starting material and functionalized alkene used to obtain each of the compounds listed in Table 2 are set forth in Table 1.

TABLE 1

Nucleosides which have been synthesized by this method.

Starting Material: Nucleoside 1

Nucleoside 2

Nucleoside 3

| Product ID No. | Nucleoside Starting Material | X | Functionalized Alkene | Yield (%) |
|---|---|---|---|---|
| 1 | 1 | I | but-3-en-2-ol | 98 |
| 2 | 1 | I | pent-4-en-2-ol | 96 |
| 3 | 1 | I | hex-5-en-2-one | 82 |
| 4 | 1 | I | allyl alcohol | 71 |
| 5 | 1 | I | pent-4-en-1-ol | 79 |
| 6 | 1 | I | undec-10-en-1-ol | 98 |
| 7 | 2 | I | hex-5-en-1-ol | 88 |
| 8 | 3 | I | hex-5-en-1-ol | 61 |
| 9 | 3 | I | pent-4-en-2-ol | 82 |
| 10 | 3 | I | but-3-en-2-ol | 45 |
| 11 | 3 | I | allyl alcohol | 37 |
| 12 | 3 | I | hex-5-en-2-one | 50 |
| 13 | 3 | I | but-3-en-1-ol | 100 |

TABLE 2
Modified Nucleosides.
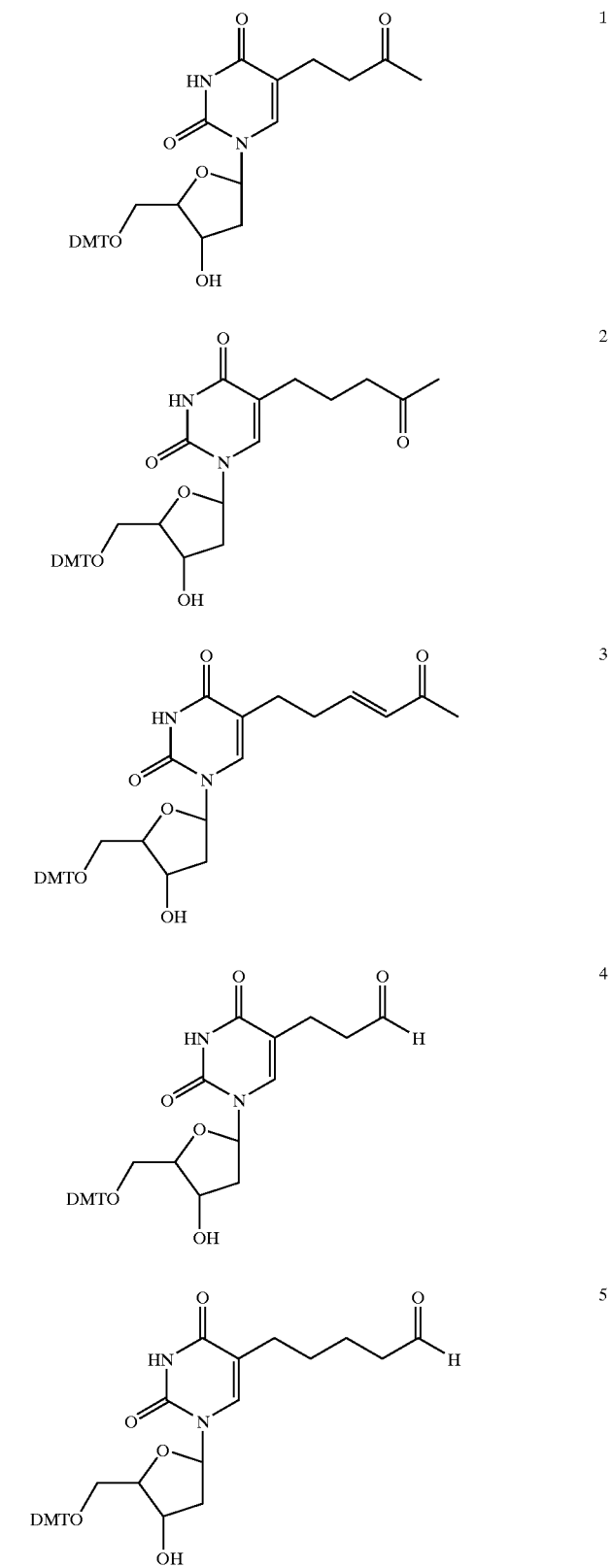

TABLE 2-continued
Modified Nucleosides.
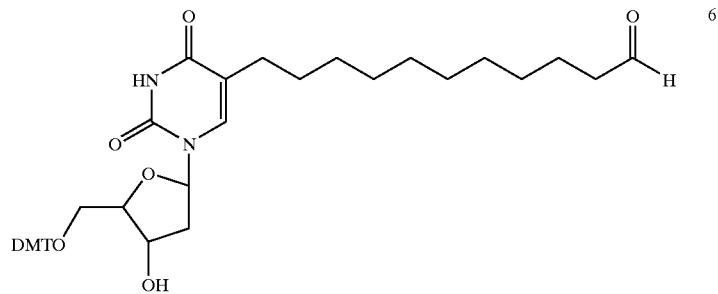
6
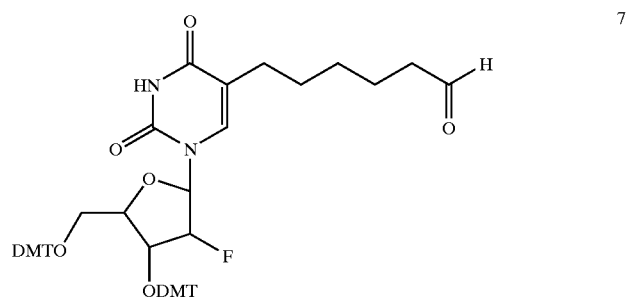
7
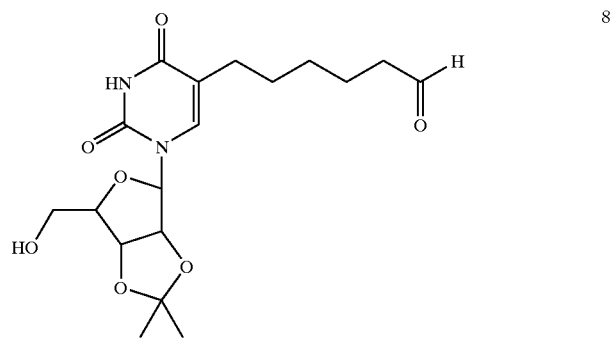
8
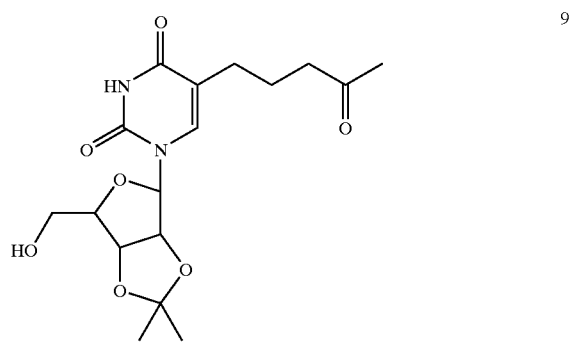
9

TABLE 2-continued

Modified Nucleosides.

| | |
|---|---|
| (structure of compound 10: thymine-like base with 3-oxobutyl side chain at C5, attached to isopropylidene-protected ribofuranose with 5'-OH) | 10 |
| (structure of compound 11: uracil with 3-oxopropyl (propanal) side chain at C5, attached to isopropylidene-protected ribofuranose with 5'-OH) | 11 |
| (structure of compound 12: uracil with 5-oxo-3-hexenyl side chain at C5, attached to isopropylidene-protected ribofuranose with 5'-OH) | 12 |
| (structure of compound 13: uracil with 4-oxobutyl (butanal) side chain at C5, attached to isopropylidene-protected ribofuranose with 5'-OH) | 13 |

Characterization of Modified Nucleosides.

Compound 1.

$^1$H NMR (CDCl$_3$) δ1.88 (s, 3 H), 1.98–2.33 (m, 3 H), 2.40 (m, 3 H), 3.31 (m, 1 H), 3.43 (m, 1 H), 3.76 (s, 6 H), 4.02 (m, 1 H), 4.52 (m, 1 H), 6.36 (m, 1 H), 6.80 (d, J=8.7 Hz, 4 H), 7.24 (m, 7 H), 7.38 (m, 2 H), 8.07 (s, 1 H).

Compound 2.

(Contains 14% isomer) $^1$H NMR (CDCl$_3$) δ1.49 (m, 2 H), 1.72 (m, 1 H), 1.88 (m, 1 H), 1.97 (s, 3 H), 2.10 (t, J=7.5 Hz, 2 H), 2.36 (m, 2 H), 2.96 (br s, 1 H), 3.20 (m, 1 H), 3.45 (m, 1 H), 3.76 (s, 6 H), 4.03 (m, 1 H), 4.54 (m, 1 H), 6.41 (m, 1 H), 6.81 (d, J=8.7 Hz, 4 H), 7.24 (m, 7 H), 7.36 (m, 2 H), 7.52 (s, 1 H), 9.21 (br s, 1 H).

Compound 3.

¹H NMR (CDCl₃) δ1.86–2.23 (m, 4 H), 2.12 (s, 3 H), 2.23–2.48 (m, 2 H), 2.92 (br s, 1 H), 3.32 (m, 1 H), 3.50 (m, 1 H), 3.75 (s, 6 H), 4.06 (m, 1 H), 4.58 (m, 1 H), 5.72 (d, J=15.9 Hz, 1 H), 6.43 (m, 2 H), 6.80 (d, J=8.1 Hz, 4 H), 7.25 (m, 7 H), 7.37 (m, 2 H) 7.61 (m, 1 H), 9.28 (br s, 1 H).

Compound 4.

(Contains 16% isomer) ¹H NMR (CDCl₃) δ2.06 (m, 2 H), 2.35 (m, 4 H), 3.32 (m, 1 H), 3.44 (m, 1 H), 3.74 (s, 6 H), 4.05 (m, 1 H), 4.54 (m, 1 H), 6.69 (m, 1 H), 6.79 (d, J=8.9 Hz, 4 H), 7.12–7.41 (m, 9 H), 7.57 (s, 1 H), 9.45 (s, 1 H).

Compound 5.

(Contains 25% isomer) ¹H NMR (CDCl₃) δ1.25 (m, 2 H), 1.79 (m, 2 H), 1.87 (m, 2 H), 2.07 (m, 2 H), 2.25–2.47 (m, 2 H), 3.28 (m, 1 H), 3.49 (m, 1 H), 3.76 (s, 6 H), 4.05 (m, 1 H), 4.57 (m, 1 H), 6.42 (m, 1 H), 6.80 (d, J=8.6 Hz, 4 H), 7.24 (m, 7 H), 7.36 (m, 2 H), 7.55 (s, 1 H), 8.86 (s, 1 H), 9.54 (s, 1 H).

Compound 6.

(Contains 22% isomer) ¹H NMR (CDCl₃) δ0.82–1.34 (m, 14 H), 1.58 (m, 2 H), 1.74 (m, 1 H), 1.92 (m, 1 H), 2.12–2.50 (m, 4 H), 2.55 (m, 1 H), 3.32 (m, 1 H), 3.52 (m, 1 H), 3.76 (s, 6 H), 4.04 (m, 1 H), 4.54 (m, 1 H), 6.40 (m, 1 H), 6.81 (d, J=8.5 Hz, 4 H), 7.18–7.43 (m, 9 H), 7.47 (s, 1 H), 9.11 (s, 1 H), 9.73 (s, 1 H).

Compound 8.

(Contains 29% isomer) ¹H NMR (CDCl₃) δ1.17–1.68 (m, 6 H), 1.31 (s, 3 H), 1.53 (s, 3 H), 2.25 (m, 2 H), 2.41 (m, 2 H), 3.81 (m, 2 H), 4.23 (m, 1 H), 4.93 (m, 1 H), 4.99 (m, 1 H), 5.57 (d, J=2.8 Hz, 1 H), 7.17 (s, 1 H), 9.71 (s, 1 H).

Compound 9.

(Contains 15% isomer) ¹H NMR (CDCl₃) δ1.33 (s, 3 H), 1.56 (s, 3 H), 1.77 (m, 2 H), 2.13 (s, 3 H), 2.28 (t, J=7.8 Hz, 2 H), 2.45 (t, J=7.1 Hz, 2 H), 3.47 (s, 1 H), 3.79 (m, 1 H), 3.91 (m, 1 H), 4.23 (m, 1 H), 4.92 (m, 1 H), 5.67 (d, J=1.9 Hz, 1 H), 7.33 (s, 1 H), 9.33 (s, 1 H).

Compound 10.

(Contains 12% isomer) ¹H NMR (CDCl₃) δ1.32 (s, 3 H), 1.55 (s, 3 H), 2.09 (s, 3 H), 2.52 (t, J=6.3 Hz, 2 H), 2.72 (t, J=6.3 Hz, 2 H), 3.78 (dd, J=3.0, 12.2 Hz, 1 H), 3.93 (dd, J=2.1, 12.2 Hz, 1 H), 4.28 (m, 1 H), 4.93 (m, 2 H), 5.70 (d, J=2.1 Hz, 1 H), 7.47 (s, 1 H), 9.53 (s, 1 H).

Compound 11.

(Contains 23% isomer) ¹H NMR (CDCl₃) δ1.33 (s, 3 H), 1.55 (s, 3 H), 2.59 (t, J=6.4 Hz, 2 H), 2.77 (t, J=6.4 Hz, 2 H), 3.78 (m, 1 H), 3.91 (m, 1 H), 4.28 (m, 1 H), 4.92 (m, 2 H), 5.65 (d, J=2.5 Hz, 1 H), 7.43 (s, 1 H), 9.72 (s, 1 H).

Compound 12.

(Contains 27% isomer) ¹H NMR (CDCl₃) δ1.33 (s, 3 H), 1.56 (s, 3 H), 2.22 (s, 3 H), 2.49 (m, 4 H), 3.59 (s, 1 H), 3.78 (m, 1 H), 3.90 (m, 1 H), 4.29 (m, 1 H), 4.91 (m, 2 H), 5.71 (d, J=2.3 Hz, 1 H), 6.12 (d, J=15.9 Hz, 1 H), 6.75 (m, 1 H), 7.33 (s, 1 H), 8.96 (s, 1 H).

Compound 13.

(Contains 26% isomer) ¹H NMR (CDCl₃) δ1.34 (s, 3 H), 1.57 (s, 3 H), 1.85 (m, 2 H), 2.32 (m, 2 H), 2.48 (m, 2 H), 3.80 (m, 1 H), 4.92 (m, 1 H), 4.28 (m, 1 H), 4.97 (m, 2 H), 5.62 (d, J=2.7 Hz, 1 H), 7.27 (s, 1 H), 9.74 (s, 1 H).

What is claimed is:

1. An oligonucleotide comprising a purine nucleoside modified at the 2-, 6- or 8-position of the purine ring prepared according to a method comprising comprising the steps of:

reacting a purine starting material containing a leaving group attached to the 2-, 6- or 8-position of said purine starting material with a functionalized alkene having the formula:

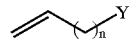

wherein

Y is selected from the group consisting of —CHROH, —C(O)R, —COOR, —C(O)NRR', —CN, a substituted or unsubstituted aryl group or heterocylic group, selected from the group consisting of phenyl, 2-,3- or 4-hydroxyphenyl, 2-,3- or 4-pyridyl and 1H-tetrazol-5-yl;

R and R' are independently selected from the group consisting of H, substituted or unsubstituted alkyl, alkenyl and aryl; and n is an integer from 0–15 in the presence of a palladium catalyst of the general formula PdL₃ or PdL₄, wherein L is a ligand of palladium; and isolating said modified nucleoside or nucleotide.

2. The oligonucleotide of claim 1 wherein said oligonucleotide is a ribonucleic acid.

3. The oligonucleotide of claim 1 wherein said oligonucleotide is a deoxyribonucleic acid.

4. An oligonucleotide comprising a pyrimidine nucleoside modified at the 5-or 6-position of the pyrimidine ring prepared according to a method comprising the steps of:

reacting a pyrimidine starting material containing a leaving group attached to the 5- or 6-position of said pyrimidine starting material with a functionalized alkene having the formula:

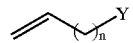

wherein

Y is selected from the group consisting of —C(O)R, —COOR, —C(O)NRR', —CN, phenyl, 2-, 2- or 4-hydroxyphenyl, 2-,3- or 4-pyridyl and 1H-tetrazol-5-yl;

R and R' are independently selected from the group consisting of H, alkyl, alkenyl and aryl; and n is an integer from 1–15 in the presence of a palladium catalyst of the general formula PdL₃ or PdL₄, wherein L is a ligand of palladium to produce a pyrimidine nucleoside having the following formula:

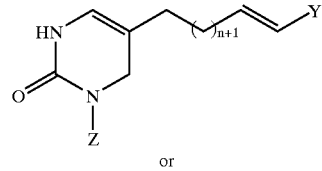

or

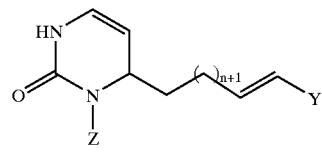

wherein

Z is selected from the group consisting of H, ribose, deoxyribose, dideoxyribose and derivatives thereof; and isolating said modified nucleoside.

5. The oligonucleotide of claim 4 wherein said oligonucleotide is a ribonucleic acid.

6. The oligonucleotide of claim 4 wherein said oligonucleotide is a deoxyribonucleic acid.

7. An oligonucleotide comprising a pyrimidine nucleoside modified at the 5-or 6-position of the pyrimidine ring prepared according to a method comprising the steps of:

reacting a pyrimidine starting material containing a leaving group attached to the 5- or 6-position of said pyrimidine starting material with a functionalized alkene having the formula:

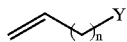

wherein

Y is CHROH;

R is independently selected from the group consisting of H, alkyl, alkenyl and aryl; and n is an integer from 0–15 in the presence of a palladium catalyst of the general formula $PdL_3$ or $PdL_4$, wherein L is a ligand of palladium to produce a pyrimidine nucleoside having the following formula:

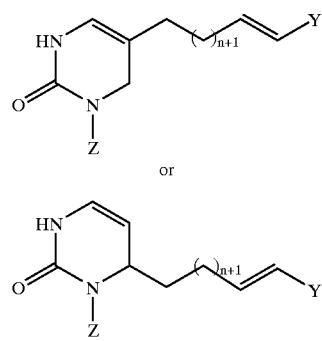

wherein

Z is selected from the group consisting of H, ribose, deoxyribose, dideoxyribose and derivatives thereof; and isolating said modified nucleoside.

8. The oligonucleotide of claim 7 wherein said oligonucleotide is a ribonucleic acid.

9. The oligonucleotide of claim 7 wherein said oligonucleotide is a deoxyribonucleic acid.

* * * * *